(12) United States Patent
DeRidder et al.

(10) Patent No.: US 8,523,767 B2
(45) Date of Patent: Sep. 3, 2013

(54) ADD-ON RETRACTOR ELEMENT FOR RETRACTOR SYSTEM

(75) Inventors: Steven D. DeRidder, Bartlett, TN (US); Charles S. Sullivan, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 49 days.

(21) Appl. No.: 13/161,661

(22) Filed: Jun. 16, 2011

(65) Prior Publication Data

US 2012/0323080 A1     Dec. 20, 2012

(51) Int. Cl.
*A61B 1/32* (2006.01)

(52) U.S. Cl.
USPC .......................................... 600/208; 600/215

(58) Field of Classification Search
USPC ............... 600/208, 210, 224, 214, 219, 220, 600/222, 223, 225, 228, 229, 215; 606/198
See application file for complete search history.

(56) References Cited

U.S. PATENT DOCUMENTS

| | | | |
|---|---|---|---|
| 3,841,317 A * | 10/1974 | Awais | 600/203 |
| 6,036,638 A * | 3/2000 | Nwawka | 600/186 |
| 6,354,995 B1 | 3/2002 | Hoftman et al. | |
| 6,432,048 B1 * | 8/2002 | Francois | 600/220 |
| 6,902,530 B1 * | 6/2005 | Pianka | 600/220 |
| 7,261,688 B2 | 8/2007 | Smith et al. | |
| 7,481,766 B2 | 1/2009 | Lee et al. | |
| 7,594,888 B2 * | 9/2009 | Raymond et al. | 600/219 |
| 7,618,367 B2 | 11/2009 | Martin et al. | |
| 2003/0191371 A1 | 10/2003 | Smith et al. | |
| 2005/0080320 A1 | 4/2005 | Lee et al. | |
| 2005/0159650 A1 | 7/2005 | Raymond et al. | |
| 2006/0106416 A1 | 5/2006 | Raymond et al. | |
| 2007/0021656 A1 | 1/2007 | Martin et al. | |
| 2007/0118023 A1 | 5/2007 | Smith et al. | |
| 2007/0123753 A1 * | 5/2007 | Abdelgany et al. | 600/220 |
| 2007/0225568 A1 | 9/2007 | Colleran | |
| 2007/0270655 A1 | 11/2007 | Smith et al. | |
| 2008/0033251 A1 | 2/2008 | Araghi | |
| 2008/0146885 A1 * | 6/2008 | Protopsaltis | 600/210 |
| 2008/0188718 A1 | 8/2008 | Spitler et al. | |
| 2010/0217088 A1 | 8/2010 | Heiges et al. | |

* cited by examiner

*Primary Examiner* — Pedro Philogene

(57) ABSTRACT

A retractor assembly for percutaneous surgery in a patient that includes first and second retractor portions positionable opposite one another in an incision of the patient. A working channel extends between the first and second retractor portions and provides access to a location within the patient adjacent to distal ends of the first and second retractor portions. The first and second retractor portions are movable relative to one another to adjust the size of the working channel. An add-on retractor element is provided that is mounted to the first and second retractor portions and spans the gap between the first and second retractor portions to prevent creep of soft tissue into the working channel when the retractor portions are separated.

18 Claims, 6 Drawing Sheets

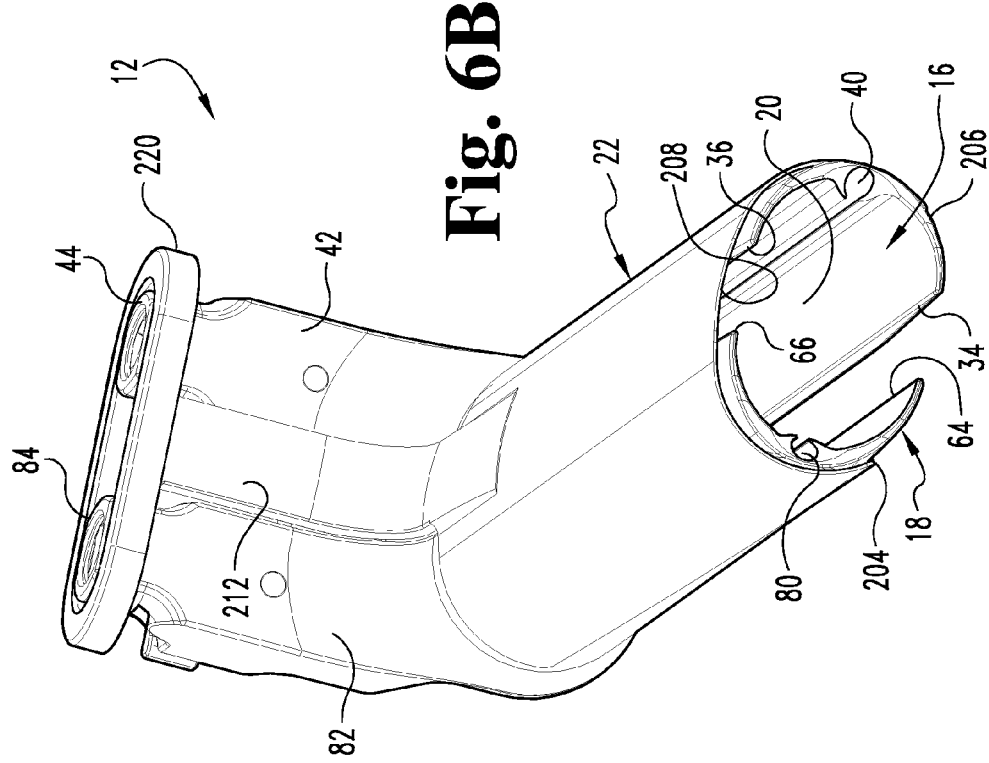
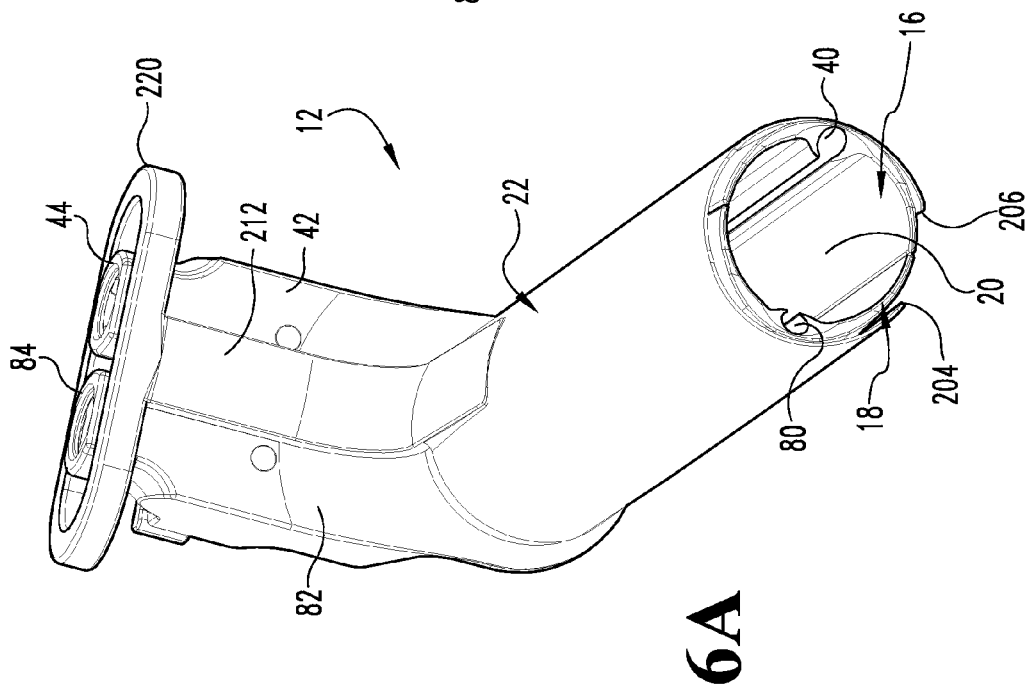

ADD-ON RETRACTOR ELEMENT FOR RETRACTOR SYSTEM

BACKGROUND

The present application relates to tissue retraction to facilitate a procedure, such as minimally invasive surgery, within a patient.

Traditional surgical procedures for pathologies located within the body can cause significant trauma to the intervening tissues. These procedures often require a long incision, extensive muscle stripping, prolonged retraction of tissues, denervation and devascularization of tissue. These procedures can require operating room time of several hours and several weeks of post-operative recovery time due to the destruction of tissue during the surgical procedure. In some cases, these invasive procedures lead to permanent scarring and pain that can be more severe than the pain leading to the surgical intervention.

The development of percutaneous procedures has yielded a major improvement in reducing recovery time and post-operative pain because minimal dissection of tissue, such as muscle tissue, is required. For example, minimally invasive surgical techniques are desirable for spinal and neurosurgical applications because of the need for access to locations within the body and the danger of damage to vital intervening tissues. In one form, access to locations within the body is provided by a working channel between oppositely positioned retractor blades. If necessary, the retractor blades can be moved relative to one another to adjust the size of the working channel. However, when the retractor blades are displaced away from one another to enlarge the working channel for example, tissue surrounding the retractor blades can encroach into the working channel, interfering with visualization by the surgeon and obstructing access to the location within the body. Thus, while developments in minimally invasive surgery are steps in the right direction, there remains a need for further developments in minimally invasive surgical instruments and methods.

SUMMARY

One nonlimiting embodiment of the present application is directed to a retractor assembly for percutaneous surgery in a patient that includes first and second retractor portions positionable opposite one another in an incision of the patient. A working channel extends between the first and second retractor portions and provides access to a location within the patient adjacent to distal ends of the first and second retractor portions. The first and second retractor portions are movable relative to one another to adjust the size of the working channel. In addition, an add-on retractor element extends between the first and second retractor portions and spans the gap between the first and second retractor portions as the first and second retractor portions are separated from one another. The add-on retractor element is flexible to wrap at least partially around the first and second retractor portions and unroll as the first and second retractor portions are separated. The add-on retractor element prevents tissue creep into the space between the retractor portions. However, in other embodiments, different forms and applications are envisioned.

Another nonlimiting embodiment of the present application is directed to a retractor assembly for percutaneous surgery in a patient that includes first and second retractor portions positionable opposite one another in an incision of the patient. A working channel extends between the first and second retractor portions and provides access to a location within the patient adjacent to distal ends of the first and second retractor portions. The first and second retractor portions are movable relative to one another to adjust the size of the working channel. The first and second retractor portions each include an extension extending laterally from a proximal end thereof for engagement to a rack system that allows application of separation forces for the retractor portions through the extensions. An add-on retractor element includes a body member that extends between the first and second retractor portions and spans the gap between the first and second retractor portions as the first and second retractor portions are separated from one another. The proximal end of the add-on retractor element includes a mounting structure that is mountable to the extensions of the first and second retractor portions. In one specific embodiment, the mounting structure limits movement of the first and second retractor portions away from one another so that the retraction portion of the add-on retractor element is maintained in engagement with the first and second retractor portions. However, in other embodiments, different forms and applications are envisioned.

Another embodiment of the present application is a unique apparatus for percutaneous surgery in a patient. Other embodiments include unique methods, systems, devices, kits, assemblies, equipment, and/or apparatus involving a retractor assembly with an add-on retractor element to prevent tissue creep between retractor portion of the retractor assembly.

Further embodiments, forms, features, aspects, benefits, objects and advantages of the present application shall become apparent from the detailed description and figures provided herewith.

BRIEF DESCRIPTION OF THE FIGURES

FIG. 6A is a perspective view looking toward the retractor assembly illustrated in FIG. 2 in an unexpanded configuration.

FIG. 6B is a perspective view looking toward the retractor assembly illustrated in FIG. 2 in an expanded configuration.

DESCRIPTION OF THE ILLUSTRATED EMBODIMENTS

Figure 1:
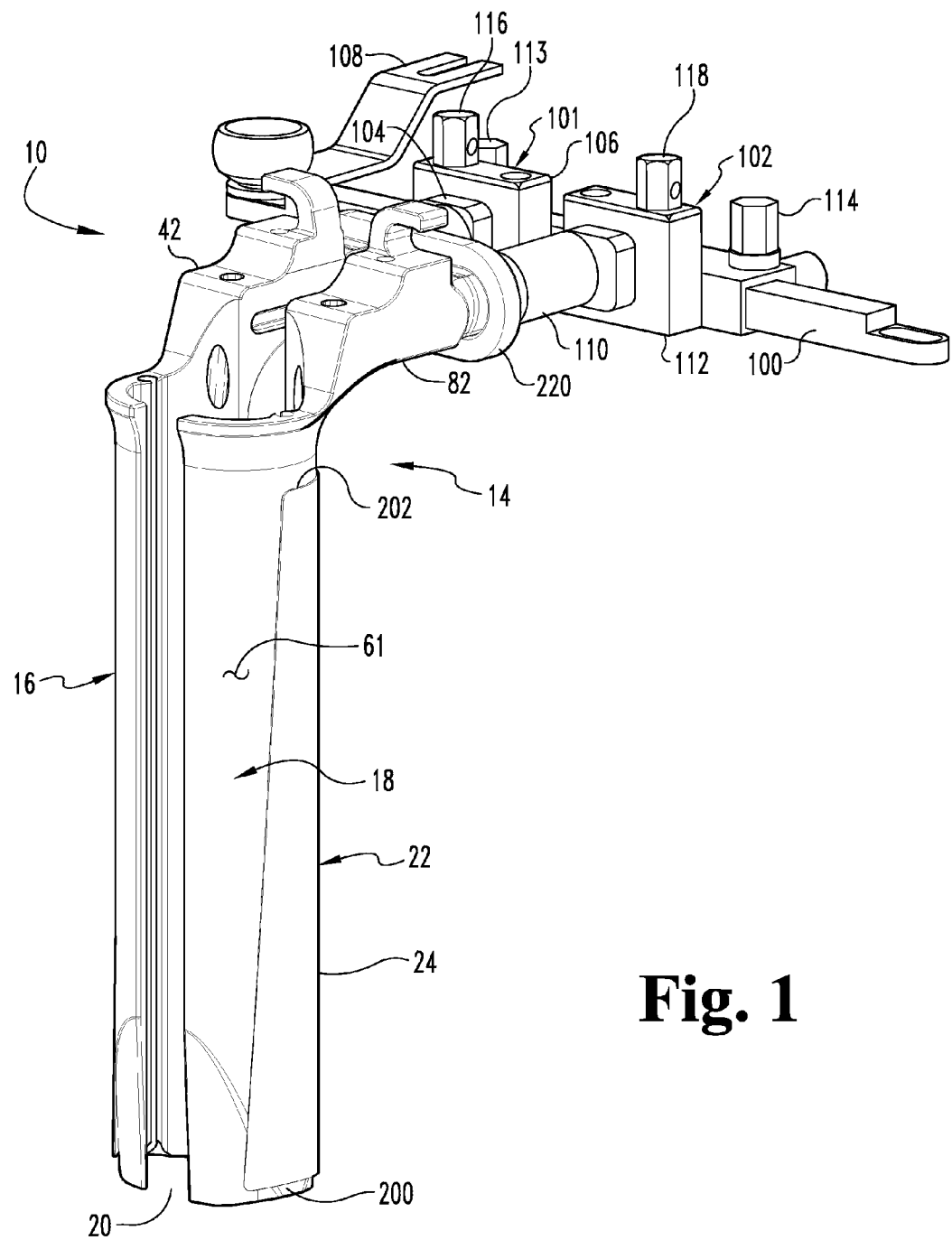
FIG. 1 is a perspective view of a retractor system in an expanded configuration.
Figure 2:
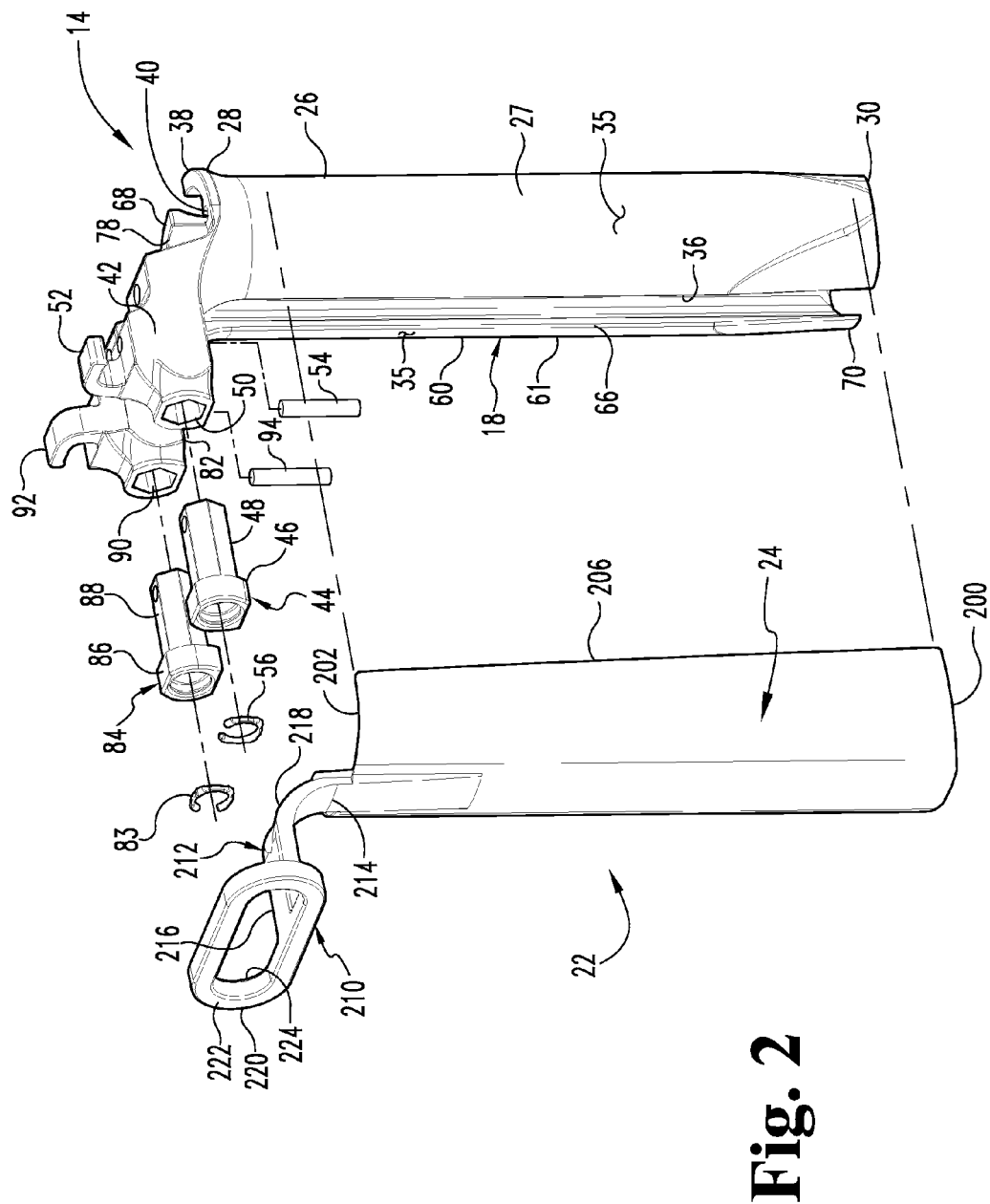
FIG. 2 is an exploded view of a retractor assembly of the retractor system illustrated in FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

Surgical instruments, systems and methods for performing percutaneous surgery, including spinal surgeries that include one or more techniques such as laminotomy, laminectomy, foramenotomy, facetectomy, discectomy, interbody fusion, spinal nucleus or disc replacement, and implant insertion including plates, rods, and bone engaging fasteners, for example, are provided. The surgery is performed through a working channel or passageway through skin and tissue of the patient provided by a retractor assembly. The retractor assembly comprises a portion of a retractor system that allows the working channel or passageway to be increased in size by moving retractor portions of the retractor assembly away from one another by translation, pivoting, or combinations thereof. The retractor assembly is movable in situ to increase the size of the working channel to facilitate access to the working space at the distal end of the retractor assembly while minimizing trauma to tissue surrounding the retractor and preventing tissue creep into the working channel along at least one side of the retractor portions. Viewing of the surgical site at the working end of the retractor assembly can be accomplished with viewing instruments mounted on the retractor assembly, positioned over the retractor assembly, positioned in other portals in the body, and/or through a viewing system such as lateral fluoroscopy. The retractor system can be used with any surgical approach to the spine, including anterior, posterior, posterior mid-line, lateral, postero-lateral, and/or antero-lateral approaches, and in other regions besides the spine.

Referring now generally to FIG. 1, there is illustrated one embodiment retractor system 10 in an expanded configuration. Retractor system 10 includes a separation instrument 12 positionable outside the patient and a retractor assembly 14 movably mounted to mounting structure 12. Retractor assembly 14 includes a first retractor portion 16 positioned opposite of a second retractor portion 18 extending along and around a central longitudinal axis L1. A working channel 20 is positioned between first and second retractor portions 16, 18. Although two retractor portions 16, 18 are shown in the illustrated embodiment, more than two retractor portions are also contemplated. Retractor assembly 14 further includes an add-on retractor member 22 mounted to the proximal end structure of retractor portions 16, 18. Add-on retractor member 22 includes an elongated body portion 24 that extends along and between retractor portions 16, 18 to prevent tissue migration into working channel 20 between retractor portions 16, 18 when retractor portions 16, 18 are moved away from the unexpanded configuration toward the expanded configuration. Typically, in spinal surgery, add-on retractor member 22 is placed on the contralateral side of retractor assembly 14, although placement on other sides of retractor assembly 14 and relative to the patient are contemplated.

With further reference to FIGS. 2-6, first retractor portion 16 is generally in the form of a retractor blade and includes an elongate body 26 having a sidewall 27 extending between a proximal end 28 and an opposite distal end 30. Sidewall 27 of elongate body 26 further extends between oppositely positioned longitudinal edges 34, 36 (FIG. 6B) which extend between proximal and distal ends 28, 30. In the illustrated embodiment, edges 34, 36 are linear between proximal end 28 and distal end 30 and extend parallel to one another and parallel to longitudinal axis L1, although non-parallel and non-linear arrangements are not precluded.

Proximal end 28 includes a rim 38 that extends laterally outwardly from sidewall 27 at proximal end 28. However, forms in which rim 38 is not provided are also contemplated. Rim 38 also defines a passage 40 opening proximally and distally therethrough and that also extends along the inner surface of retractor portion 16 to distal end 30 receive a pin or other structure to secure retractor portion 16 to bone. However, embodiments in which passage 40 is omitted are also contemplated.

Extending proximally and laterally from proximal end 28 of elongate body 26 is a first extension 42 including a foot 44 removably engageable to separation instrument 12 by C-clip 56 positioned in the end opening of foot 44. In the illustrated embodiment, foot 44 includes an enlarged outer portion 46 defining the end-opening and a smaller cross-section shaft portion 48 that is received in a receptacle 50 that opens at the outer end of first extension 42. First extension 42 also includes a hook portion 52 extending proximally therefrom configured to engage with one or more other surgical instruments, non-limiting examples of which will be provided below, or with an external arm that supports retractor assembly 14 while positioned in the patient. For the sake of clarity, it should be appreciated that foot 44 is releasably coupled with first extension 42 in the illustrated embodiment with pin 54. In addition, it should be appreciated that first extension 42 may be releasably or non-releasably coupled with elongate body 26, and in some alternative, non-illustrated forms may be absent from first retractor portion 16. It should be appreciated that distal end 30 is slightly beveled to facilitate insertion of first retractor portion 16 into an incision, although non-beveled forms for distal end 30 are also contemplated.

Furthermore, in the illustrated embodiment, sidewall 27 is generally linear in the direction of longitudinal axis L1 and is generally arcuately shaped around longitudinal axis L1 such that elongate body 26 has a generally u-shaped cross section when viewed looking on and in the direction of longitudinal axis L1. Other cross-sectional shapes are also contemplated for sidewall 27, such as, for example, any linear, open sided polygonal shape, or combined curved/polygonal shape, just to provide a few examples.

First retractor portion 16 can be provided with sufficient rigidity between proximal and distal ends 28, 30 to separate and maintain separation of adjacent tissue when first and second retractor portions 16, 18 are initially inserted and also when the adjacent tissue is retracted by moving first retractor portion 16 and second retractor portion 18 away from one another. For example, first retractor portion 16 can include a thickness which provides sufficient rigidity to resist bending or bowing under the forces exerted on it by the retracted tissue and/or muscle. Also, the generally semicircular or u-shaped cross-section of first retractor portion 16 can be configured to provide a sufficient section modulus or moment of inertia in the direction of movement of first retractor portion 16 to resist bending, bowing and/or deflection forces applied during such movement.

Second retractor portion 18 is generally in the form of a retractor blade and includes an elongate body 60 having a sidewall 61 extending between a proximal end 68 and an opposite distal end 70. Sidewall 61 of elongate body 60 further extends between oppositely positioned longitudinal edges 64, 66 which extend between proximal and distal ends 68, 70. In the illustrated embodiment, edges 64, 66 are linear between proximal end 68 and distal end 70 and extend parallel to one another and parallel to longitudinal axis L1, although non-parallel and non-linear arrangements are not precluded.

Proximal end 68 includes a rim 78 that extends laterally outwardly from sidewall 61 at proximal end 68. However, forms in which rim 78 is not provided are also contemplated. Rim 78 also defines a passage 80 opening proximally and distally therethrough along the inner surface of retractor portion 18 to distal end 70 to receive a pin or other structure to secure retractor portion 18 to bone. However, embodiments in which passage 80 is omitted are also contemplated.

Extending proximally and laterally from proximal end 68 of elongate body 60 is a second extension 82 including a foot 84 removably engageable to separation instrument 12 by C-clip 83 positioned in the end opening of foot 84. In the illustrated embodiment, foot 84 includes an enlarged outer portion 86 and a smaller cross-section shaft portion 88 that is received in a receptacle 90 opening at the outer end of second extension 82. Second extension 82 also includes a hook portion 92 projecting proximally therefrom that is configured to engage with one or more other surgical instruments, non-limiting examples of which will be provided below, or with an external arm that supports retractor assembly 14 while positioned in the patient. For the sake of clarity, it should be appreciated that foot 84 is releasably coupled with second extension 82 in the illustrated embodiment with pin 94. In addition, it should be appreciated that second extension 82 may be releasably or non-releasably coupled with elongate body 60, and in some alternative, non-illustrated forms may be absent from second retractor portion 18. Distal end 70 can also be slightly beveled to facilitate insertion of second retractor portion 18 into an incision, although non-beveled forms for distal end 70 are also contemplated.

In the illustrated embodiment, sidewall 61 is generally linear in the direction of longitudinal axis L1 and is generally arcuately shaped around longitudinal axis L1 such that elongate body 60 has a generally u-shaped cross section when viewed looking on and in the direction of longitudinal axis L1. Other cross-sectional shapes are also contemplated for sidewall 61, such as, for example, any linear, open sided polygonal shape, or combined curved/polygonal shape, just to provide a few examples.

Second retractor portion 18 can be provided with sufficient rigidity between proximal and distal ends 68, 70 to separate and maintain separation of adjacent tissue when first and second retractor portions 16, 18 are initially inserted and also when the adjacent tissue is retracted by moving first retractor portion 16 and second retractor portion 18 away from one another. For example, second retractor portion 18 can include a thickness which provides sufficient rigidity to resist bending or bowing under the forces exerted on it by the retracted tissue and/or muscle. Also, the generally semicircular or u-shaped cross-section of second retractor portion 18 can be configured to provide a sufficient section modulus or moment of inertia in the direction of movement of second retractor portion 18 to resist bending, bowing and/or deflection forces applied during such movement.

In the illustrated embodiment, retractor portions 16, 18 are minor images of one another and cooperate to define working channel 20. First and second retractor portions 16, 18 are positioned with their longitudinal edges 34, 64 and longitudinal edges 36, 66 in abutting arrangement with one another when retractor portions 16, 18 are in an unexpanded configuration to facilitate insertion of first and second retractor portions 16, 18 into an incision of a patient. Other embodiments contemplate first and second retractor portions 16, 18 with their respective adjacent longitudinal edges in overlapping arrangement or slightly spaced when retractor portions 16, 18 are in the unexpanded configuration. Moreover, in the unexpanded configuration, this arrangement between first and second retractor portions 16, 18 results in external surface portion 35 of sidewall 27 being positioned adjacent to and flush with external surface 65 of sidewall 61 when retractor assembly 14 is in its insertion or unexpanded configuration. Similarly, when retractor assembly 14 is in this configuration, the outer periphery defined by first and second retractor portions 16, 18 is also generally continuous and smooth.

As indicated above, working channel 20 is formed between first and second retractor portions 16, 18. Working channel 20 extends between and opens at distal ends 30, 70 and proximal ends 28, 68. Moreover, in the unexpanded, insertion configuration, working channel 20 is peripherally surrounded or enclosed by first and second retractor portions 16, 18, and has a circular cross-sectional configuration orthogonal to longitudinal axis L1, although oblong, oval or racetrack-shaped configurations are also contemplated, among others. External surfaces 35, 65 define a similarly or identically shaped cross-section around longitudinal axis L1 as well. In addition, working channel 20 and outer surfaces 35, 65 when expanded define an oval or elongated cross-sectional shape orthogonal to longitudinal axis L1. Retractor portions 16, 18 can also define a frusto-conical configuration by pivoting distal ends 30, 70 away from one another in order to facilitate greater manipulation of instruments in working channel 20. It is also contemplated that working channel 20 may be provided with alternative shapes and configurations in other non-illustrated forms.

Add-on retractor element 22 includes elongated body member 24 with a length extending from a distal end 200 to a proximal end 202. Body member 24 also includes an unrolled width orthogonal to its length that extends from one of side edges 204 to the other side edge 206. Body member 24 is curved so that it is rolled partially around longitudinal axis L1 in the direction of side edges 204, 206 so that body member 24 includes an inner surface 208 positioned on or against outer surfaces 35, 65 of retractor portions 16, 18 in the unexpanded configuration. In addition, longitudinal side edges 204, 206 extend obliquely to longitudinal axis L1 so that the unrolled width of body member 24 is greatest at distal end 200 and tapers to a narrowest width at proximal end 202. As a result, body member 24 wraps around retractor portions 16, 18 a greater amount at distal end 200 than at proximal end 202. This allows add-on retractor element 22 to remain engaged to outer surfaces 35, 65 on translation axis T at distal end 200, while the resistance to movement of retractor portions 16, 18 by add-on element 22 on translation axis T is reduced by having a smaller width proximal end 202. In addition, the wider distal end of body member 24 allows body member 24 to remain engaged to outer surfaces 35, 65 if one or both of the distal ends of retractor portions 16, 18 are pivoted away from one another. Add-on retractor element 22 is flexible to conform to the outer surfaces 35, 65 and to expand by unrolling as retractor portions 16, 18 are moved away from one another. As the respective adjacent longitudinal edges 34, 64 and 36, 66 of retractor portions 16, 18 are separated to create a gap therebetween, body member 24 spans the gap between edges 36, 66 to prevent tissue creep or migration into working channel 20. Body member 24 is also elastic to roll around longitudinal axis L1 and return to its initial, unexpanded configuration as retractor portions 16, 18 are moved toward one another to their unexpanded configuration.

Add-on retractor element 22 also includes a connection portion 210 extending proximally and laterally from proximal end 202 to secure add-on retractor element 22 to retractor portions 16, 18. Connection portion 210 includes an arm 212 with a first, proximally extending portion 214 and a second laterally extending portion 216 connected with elbow 218. The outer lateral end of laterally extending portion 216 includes a mounting member 220 that is mountable to extensions 42, 82 of retractor portions 16, 18. Mounting member 220 includes a ring element 222 with laterally extending passage 224 to receive feet 44, 84 of extensions 42, 82 of retractor portions 16, 18. Passage 224 is elongated in a direction paralleling translation axis T to allow movement of retractor portions 16, 18 away from one another when extensions 42, 82 are positioned in passage 224. Ring element 222 defines a path of movement of retractor portions 16, 18 away from one another when extensions 42, 82 contact the opposite ends of ring element 222 in passage 224, and the length of passage 224 along translation axis T can be sized to limit translation of retractor portions 16, 18 and prevent over-retraction. Ring element 222 also maintains body member 24 of add-on retractor element 22 in longitudinal position along retractor portions 16, 18.

Figure 3B:
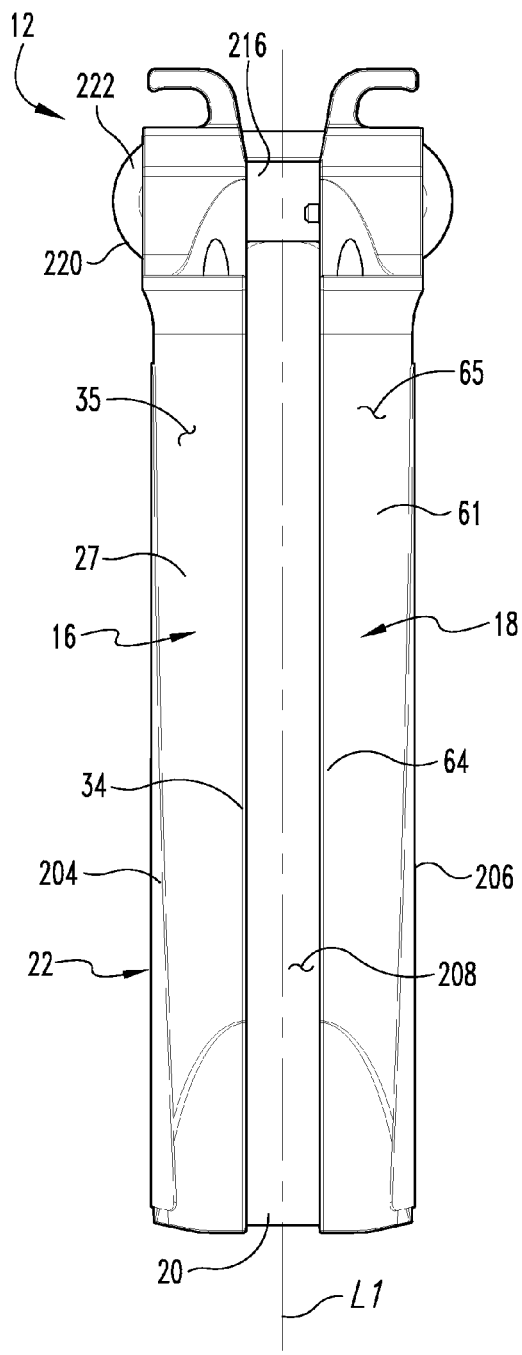
FIG. 3B is a front elevation view of the retractor assembly illustrated in FIG. 2 in an expanded configuration.
Figure 3A:
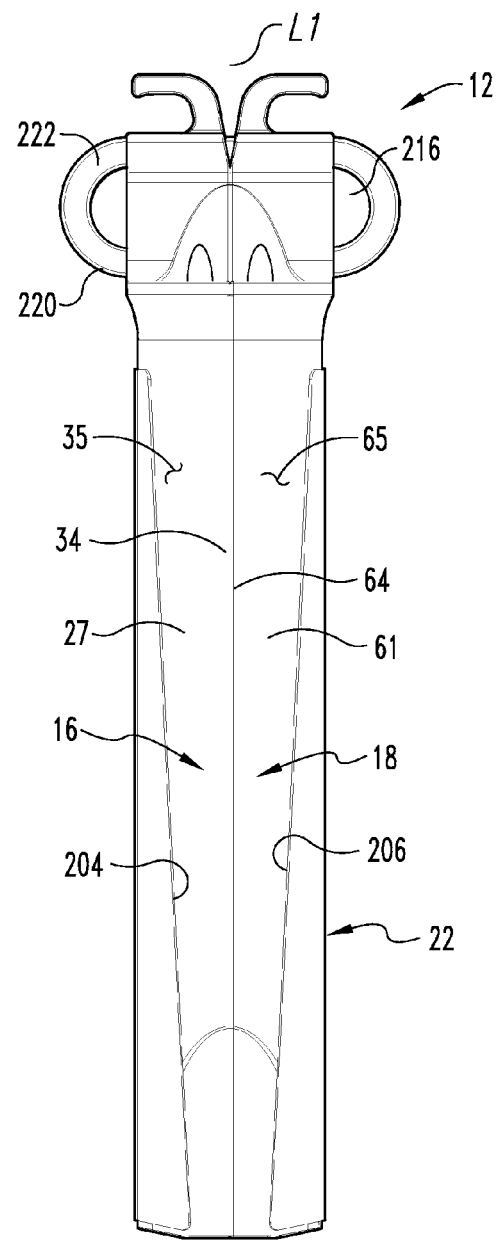
FIG. 3A is a front elevation view of the retractor assembly illustrated in FIG. 2 in an unexpanded configuration.
Figure 4:
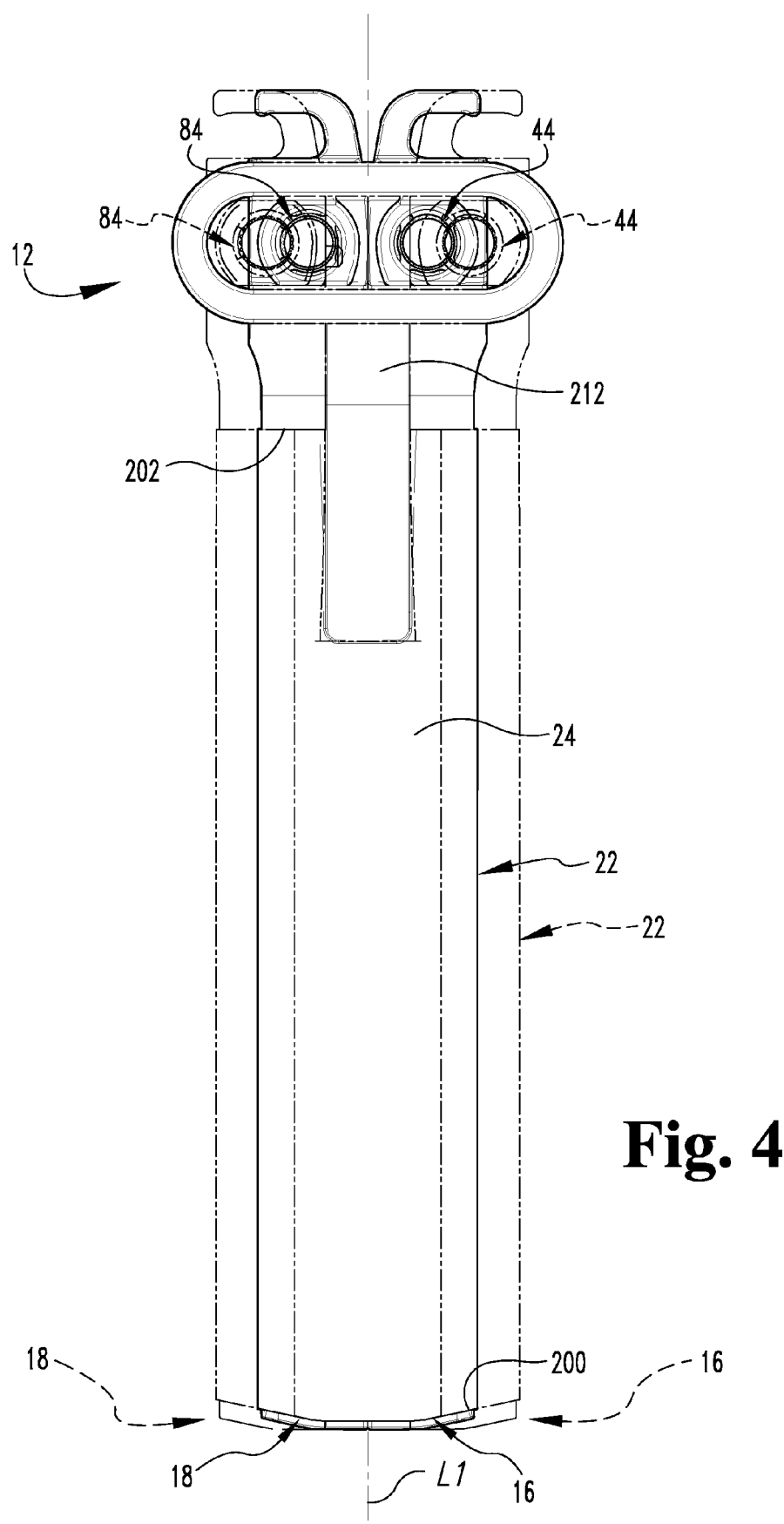
FIG. 4 is a rear elevation view of the retractor assembly illustrated in FIG. 2 showing unexpanded and expanded configurations.
Figure 5:
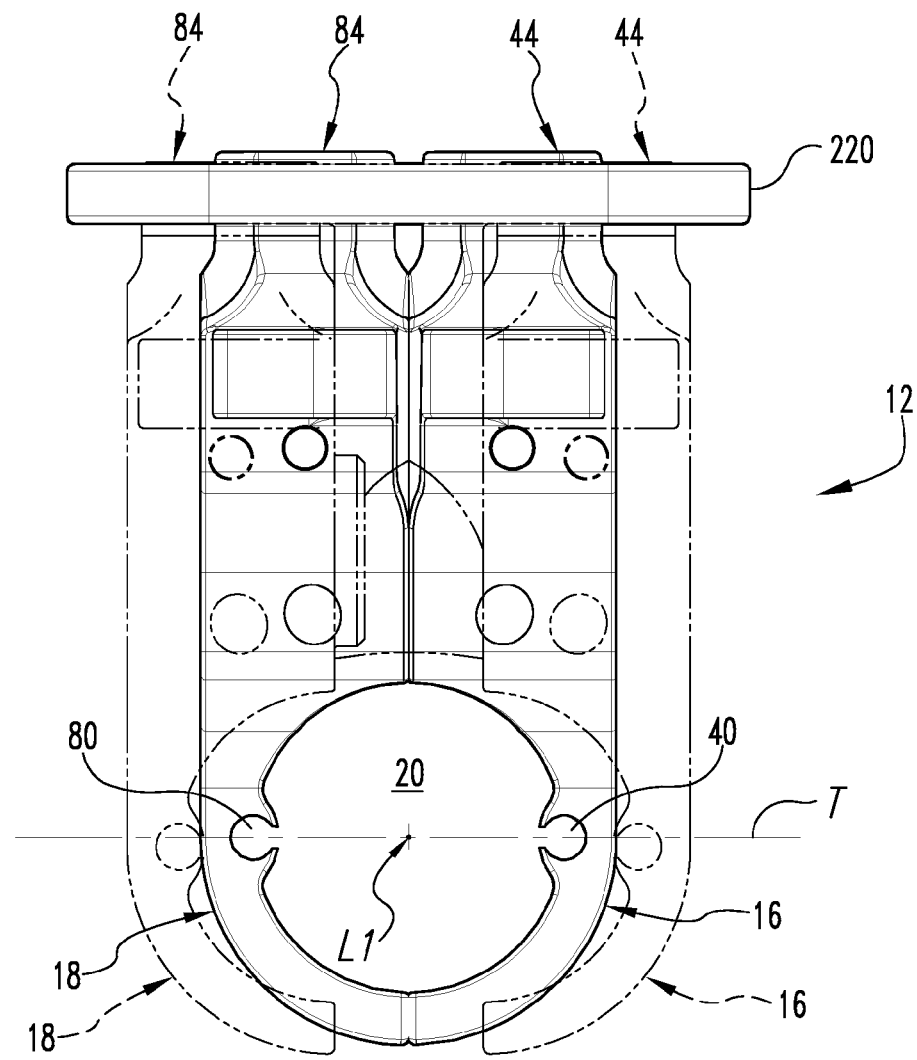
FIG. 5 is a top plan view of the retractor assembly illustrated in FIG. 2 showing unexpanded and expanded configurations.

Referring now generally to FIGS. 1, 3B, and 6B, and also in hidden lines in FIGS. 4 and 5, retractor assembly 14 is illustrated with working channel 20 enlarged from the unexpanded insertion configuration illustrated in FIGS. 3A and 6A and in solid lines shown in FIGS. 4 and 5. More particularly, first and second retractor portions 16, 18 are laterally displaced from one another along translation axis T from the unexpanded to the expanded configuration. Additionally or alternatively, first and second retractor portions 16, 18 may be pivoted toward an expanded configuration. First and second retractor portions 16, 18 are insertable through an incision in the skin and tissue of a patient to provide working channel 20 to a surgical site near distal ends 30, 70. It is contemplated that retractor portions 16, 18 are inserted through the skin and tissue in an insertion configuration for working channel 20, such as shown in FIG. 3A and FIG. 6A. Working channel 20 can have a size in the insertion configuration that allows passage of one or more surgical instruments and/or implants to the surgical site in the patient's body. It may be desirable during surgery to provide greater access to the surgical site in the patient's body beyond the locations provided through working channel 20 in its insertion configuration. Similarly, working channel 20 can be enlarged by separating first retractor portion 16 and second retractor portion 18 along translation axis T extending between first and second retractor portions 16, 18. Separation of retractor portions 16, 18 increases the size of working channel 20 from proximal ends 28, 68 to distal ends 30, 70, and can be performed with separation instrument 12, one non-limiting embodiment of which is shown in connection with FIG. 1.

As first and second retractor portions 16, 18 are laterally displaced from one another, a space is created between external surface portion 35 of sidewall 27 and external surface portion 65 of sidewall 61. Add-on retractor element 22 spans the gap between sidewalls 27, 61 so at least one side of retractor portions 16, 18 and working channel 20 remains peripherally surrounded or enclosed by first and second retractor portions 16, 18 and body member 24 of add-on element 22. Thus, retractor portions 16, 18 and add-on element 22 prevent obstruction of working channel 20 by surrounding skin and tissue when working channel 20 is moved from its insertion configuration to its expanded configuration. Moreover, it should also be appreciated that first and second retractor portions 16, 18 can be laterally displaced relative to one another to provide working channel 20 with a number of different sizes or configurations between, larger, and different from the illustrated configurations while add-on retractor element 22 prevents tissue migration or creep into working channel 20. Body member 24 is configured as a partial tube in its initial configuration so that it wraps around the external surfaces and is expandable by unrolling as retractor portions 16, 18 are moved away from one another to enlarge working channel 20. The flexibility of body member 24 maintains body member 24 in contact with the external surfaces 35, 65 of retractor portions 16, 18.

Retractor portions 16, 18 may be made from any suitable surgical instrument material, such as stainless steel, aluminum, or plastics, for example. Add-on retractor element 22 may be made from any suitable flexible material, such as spring steel, plastic, or shape memory alloy, for example. The selected materials may be sterilizable for re-use, or may be inexpensive so that the instruments are disposable.

While not illustrated, it is contemplated that retractor assembly 14 may include arrangements for aligning and releasably coupling first retractor portion 16 and second retractor portion 18 in the insertion configuration. For example, one of retractor portions 16, 18 can include one or more alignment pins which are structured to engage with a corresponding alignment aperture in the other of retractor portions 16, 18. Other arrangements are also contemplated for aligning and releasably coupling first retractor portion 16 and second retractor portion 18 to one another. Examples of such arrangements include dovetail connections, fasteners, threaded coupling members, clamping members, snap rings, compression bands, straps, ball-detent mechanisms, and releasably interlocking cams or tabs, just to name a few possibilities.

In another non-illustrated form, it is contemplated that retractor assembly 14 may be configured such that first and second retractor portions 16, 18 can be pivoted or rotated toward one another about their proximal ends to provide working channel 20 with a tapered configuration that reduces in size from the distal ends of retractor portions 16, 18 through the skin to the proximal ends of retractor portions 16, 18. A tapered working channel provides the surgeon greater access and increased visualization of the surgical site while minimizing tissue retraction. A tapered working channel 20 also allows greater angulation of instruments and implants placed through working channel 20, more selection in positioning of instruments and implants within working channel 20, and the ability to position instruments and implants adjacent the inner wall surfaces of the separated first and second retractor portions 16, 18, increasing the room available at the surgical site for multiple instruments and for orienting implants.

As indicated above, working channel 20 can be expanded as necessary by moving first and second retractor portions 16, 18 away from one another along translation axis T while add-on retractor element 22 expands to span the gap between retractor portions 16, 18. In addition, it should also be appreciated that first and second retractor portions 16, 18 can be moved toward one another along translation axis T to return working channel 20 to or toward its insertion configuration and add-on element 22 collapses around retractor portions 16, 18. One non-limiting embodiment separation instrument 12 for performing these functions in connection with retractor assembly 14 is illustrated in FIG. 1. Separation instrument 12 generally includes a lateral separator operable to linearly move first and second retractor portions 16, 18 relative to one another along axis T. The lateral separator can be selectively employed by the surgeon during the surgical procedure to adjust the size of working channel 20 and provide the tissue retraction desired for conducting the surgical procedure through working channel 20.

As shown in FIG. 1, separation instrument 12 includes a rack 100 movably coupled with a first connection portion 101 and a second connection portion 102. First connection portion 101 is structured to be releasably coupled to first retractor portion 16, and second connection portion 102 is structured to be releasably coupled to second retractor portion 18. In other forms, it is also contemplated that separation instrument 12 may be non-releasably coupled with first and second retractor portions 16, 18. When coupled therewith, first and second connection portions 101, 102 extend away from first and second retractor portions 16, 18 and away from the proximal end opening of working channel 20 to facilitate access to working channel 20 during the surgical procedure. First and second connection portions 101, 102 are operable to move first and second retractor portions 16, 18 toward and away from one another along translation axis T to separate tissue.

First connection portion 101 includes a first extension arm 104 and a first coupling member 106 and extending from an end of first extension arm 104 that receives rack 100. Second connection portion 102 includes a second extension arm 110 and a second coupling member 112 extending from an end of second extension arm 110 that receives rack 100. First and second extension arms 104, 110 are removably engaged in the end openings of respective ones of feet 44, 84 with C-clips 56, 83. A bracket member 108 extends from one end of rack 100, and is engageable by a flexible arm mounted to a surgical table, for example.

Coupling members 106, 112 each includes a passage through which rack 100 is movably received. A first adjustment mechanism 113 mounted to coupling member 106 and a second adjustment mechanism 114 mounted to second coupling member 112 include splines or teeth that engage teeth along rack 100 and are operable to translate coupling members 106, 112 along rack 100 to effect movement of first and second retractor portions 16, 18 toward and away from one another along translation axis T. In the illustrated embodiment, coupling members 106, 112 also include pivot mechanisms 116, 118, respectively, mounted thereto. Pivot mechanism 116, 118 are operable to rotate extension arms 104, 110 about their respective longitudinal axis to pivot retractor portions 16, 18.

Other configurations for the separation instrument 12 are also contemplated. Other non-limiting separation instruments which may be used with retractor assembly 14 are found in U.S. Pat. No. 7,473,222, the contents of which are incorporated herein by reference in their entirety.

One particular application for retractor system 10 is in spinal surgery. It is contemplated that, after insertion of retractor portions 16, 18, they are separated predominantly in one direction to retract muscle and tissue along axis T which extends between first and second retractor portions 16, 18. For example, first and second retractor portions 16, 18 of retractor assembly 14 can be primarily or predominantly separable in the direction of the spinal column axis. The muscle tissue adjacent the spine has a fiber orientation that extends generally in the direction of the spinal column axis. The separation of retractor portions 16, 18 of retractor assembly 14 can also separate the muscle tissue along the fibers, thus the amount of separation and the resultant tearing and trauma to the muscle tissue can be minimized. It is also contemplated in other techniques employing retractor system 10 that working channel 20 can be enlarged primarily in a direction other than along the spinal column axis or in areas other than spine.

In one example, a method for positioning retractor portions 16, 18 through skin and tissue includes making an incision through the skin adjacent the location of a surgical site. For example, in spinal surgery, the incision can be made at a vertebral level at a location that provides access to the disc space between adjacent vertebrae or to one or more vertebra through a desired approach. Prior to insertion of retractor portions 16, 18, the skin and tissue can be sequentially dilated via a dilation instrument set which can include guidewires and/or one or more tissue dilators of increasing cross-sectional size. A number of sequentially inserted dilators form a pathway through the skin and tissue to the surgical site in the patient. Once the last dilator has been inserted, retractor portions 16, 18 with add-on element 22 are positioned thereover and guided therealong through the skin and tissue. It should be appreciated that translation instrument 12 may be coupled with first and second retractor portions 16, 18 either before or after they are inserted through the skin and tissue. Once first and second retractor portions 16, 18 and add-on retractor element 22 have been inserted through the skin and tissue, the dilators can be removed to provide access to the surgical site through working channel 20.

For the entire surgery or for certain procedures during the surgery, it may be desired by the surgeon to increase the size of working channel 20 to facilitate access to the surgical site. First and second retractor portions 16, 18 of retractor assembly 14 can be separated from their insertion configuration to a separated configuration in which working channel 20 is enlarged and add-on retractor element 22 is unrolls, unwraps, slides along, or otherwise expands or reconfigures to span the gap between retractor portions 16, 18 and prevent tissue creep into working channel 20.

It should be appreciated that while direct visualization through working channel is contemplated and enhanced with retractor element 22, viewing instruments can be positioned in or adjacent to working channel 20 to facilitate surgeon viewing of the surgical site. For example, an endoscopic viewing element can be mounted on the proximal end of one of retractor portions 16, 18 with a scope portion extending along working channel 20. A microscopic viewing element can be positioned over the proximal end of one of retractor portions 16, 18 for viewing the surgical site. Other imaging techniques, such as lateral fluoroscopy or loupes, can be used alone or in combination with the endoscopic and microscopic viewing elements. It is further contemplated that other instruments can be mounted on the proximal end of one or both of retractor portions 16, 18, such as nerve root retractors, tissue retractors, forceps, cutter, drills, scrapers, reamers, separators, rongeurs, taps, cauterization instruments, irrigation and/or aspiration instruments, illumination instruments, inserter instruments, and the like for use in surgical procedures through retractor assembly 14 at the surgical site. Such viewing instruments and other instruments can be employed with working channel 20 in its initial insertion configuration and/or its enlarged configuration.

In one embodiment, a first retractor portion includes a first elongate body extending between a proximal end and an opposite distal end. The first elongate body further includes a first sidewall. A second retractor portion includes a second elongate body extending between a proximal end and an opposite distal end. The second elongate body further includes a second sidewall. An add-on retractor element extends between and connects the sidewalls of the first and second retractor portion. An adjustable working channel extends between the proximal and distal ends of the first and second elongate bodies of the first and second retractor portions, and the add-on retractor element reconfigures while maintaining engagement with the first and second retractor portions as the working channel is adjusted to span at least a portion of the gap between retractor portions to prevent tissue migration into the working channel. In one embodiment, the add-on retractor element is elastic to reconfigure to its initial configuration when the retractor portions are returned to their unexpanded configuration.

In another embodiment, a first retractor portion includes a first elongate body extending between a proximal end and an opposite distal end. The first elongate body also includes a first sidewall extending between a first pair of longitudinal edges and includes a first external surface positioned between the first longitudinal edges. A second retractor portion includes a second elongate body extending between a proximal end and an opposite distal end. The second elongate body also includes a second sidewall extending between a second pair of longitudinal edges and includes a second external surface positioned between the second longitudinal edges. A working channel extends between the proximal and distal ends of the first and second elongate bodies of the first and second retractor portions, and is adjustable upon relative movement of the first and second retractor portions. A flexible add-on retractor element is wrapped around at least a portion of the first and second sidewalls and unrolls as the working channel is manipulated from an unexpanded configuration to an expanded configuration to span the gap between adjacent longitudinal edges of the first and second elongate bodies of the retractor portions.

In still another embodiment, a method for retracting tissue for percutaneous access to a surgical site in a patient includes providing a retractor assembly including first and second retractor portions and a working channel extending therebetween with an add-on retractor element extending at least partially around the first and second retractor portions; positioning the first and second retractor portions in an incision opposite of one another; expanding the working channel from a first configuration to a second, enlarged configuration by laterally displacing the first and second retractor portions away from one another; and while expanding the working channel unrolling the add-on retractor element to span a gap between the first and second retractor portions created by expanding the working channel while maintaining the add-on retractor element in engagement with the first and second retractor portions.

The retractor assemblies, devices, apparatuses, systems and methods described herein also have application with other types of instruments and implants, and may be used in other portions of the body besides the spine. The retractor assemblies, devices, apparatuses, systems and methods described herein may also be used in surgical procedures involving animals, or in demonstrations for training, education, marketing, sales and/or advertising purposes. In addition, the retractor assemblies, devices, apparatuses, systems and methods may also be used on or in connection with a non-living subject such as a cadaver, training aid or model, or in connection with testing of surgical systems, surgical procedures, orthopedic devices and/or apparatus.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. A retractor assembly for percutaneous surgery in a patient, comprising:
    a first retractor portion including a first elongate body extending between a proximal end and an opposite distal end, said first elongate body further including a first sidewall extending between said proximal and distal ends of said first retractor portion;
    a second retractor portion including a second elongate body extending between a proximal end and an opposite distal end, said second elongate body further including a second sidewall extending between said proximal and distal ends of said second retractor portion, wherein said first and second retractor portions define a working channel therebetween and are movable away from one another to adjust a size of said working channel; and
    an add-on retractor element including a flexible body member extending partially around said first and second sidewalls, wherein said body member of said add-on retractor element spans a gap between said first and second retractor portions as said first and second retractor portions are moved away from one another to increase said size of said working channel, wherein said body member of said add-on retractor element is elongated and extends between a distal end and an opposite proximal end, said body member further including opposite sides extending from said distal end to said proximal end, wherein said opposite sides define a first width of said body member at said distal end of said body member and a second width of said body member at said proximal end of said body member, and said first width is greater than said second width.

2. The retractor assembly of claim 1, wherein said first sidewall of said first elongate body extends between a first pair of oppositely positioned longitudinal edges and said second sidewall of said second elongate body extends between a second pair of oppositely positioned longitudinal edges.

3. The retractor assembly of claim 2, wherein said body member of said add-on retractor element spans a gap between adjacent ones of said longitudinal edges of said first and second sidewalls.

4. The retractor assembly of claim 1, wherein said flexible body member of said add-on retractor element is wrapped partially around said first and second sidewalls and said flexible body member unrolls as said first and second retractor portions are moved away from one another.

5. The retractor assembly of claim 1, wherein said add-on retractor element includes a connection portion at a proximal end of said body member, said connection portion being mounted to proximal ends of said first and second retractor portions.

6. The retractor assembly of claim 5, wherein said first and second retractor portions each include an extension extending laterally from said proximal end of a respective one of said first and second elongate body and said connection portion is mounted to said extensions of said first and second retractor portions.

7. The retractor assembly of claim 6, wherein said connection portion includes an arm with a first portion extending proximally from a proximal end of said body member and a second portion extending laterally from said first portion to a mounting member of said connection portion, wherein said mounting member receives said extensions of said first and second retractor portions.

8. The retractor assembly of claim 7, wherein said mounting member includes a ring element defining an elongate passage oriented in a direction of movement of said first and second retractor portions relative to one another to increase said size of said working channel.

9. The retractor assembly of claim 1, wherein said first sidewall includes au-shaped cross-sectional configuration between a first pair of longitudinal edges and said second sidewall includes a u-shaped cross-sectional configuration between a second pair of longitudinal edges.

10. The retractor assembly of claim 1, further comprising:
a first extension extending laterally away from said proximal end of said first elongate body;
a second extension extending laterally away from said proximal end of said second elongate body; and
a separation instrument engageable with said first and second extensions and configured to move said first and second retractor portions relative to one another.

11. A method for retracting tissue for percutaneous access to a surgical site in a patient, comprising: providing a retractor assembly according to claim 1;
positioning said first and second retractor portions in an incision opposite of one another; increasing said size of said working channel by laterally displacing said first and second retractor portions away from one another; and
unrolling said flexible body member as said first and second retractor portions are laterally displaced away from one another to span said gap between adjacent edges of said first and second retractor portions.

12. The method of claim 11, further comprising position first and second extensions that extend laterally from said proximal ends of said elongate bodies of said first and second retractor portions in an elongated passage of a mounting element extending from said body member of said add-on retractor element and moving said extensions along said elongated passage as said size of said working channel is increased.

13. A retractor assembly for percutaneous surgery in a patient, comprising:
a first retractor portion including a first elongate body extending between a proximal end and an opposite distal end and including a first sidewall, said first sidewall extending between a first pair of longitudinal edges and including a first external surface positioned between said first longitudinal edges and a first internal surface opposite said first external surface;
a second retractor portion including a second elongate body extending between a proximal end and an opposite distal end and including a second sidewall, said second sidewall extending between a second pair of longitudinal edges and including a second external surface positioned between said second longitudinal edges and a second internal surface opposite said second external surface, said first and second internal surfaces defining a working channel extending between said proximal and distal ends of said first and second elongate bodies of said first and second retractor portions, said working channel being adjustable upon relative movement of said first and second retractor portions; and
an add-on retractor element extending around said first and second external surfaces, wherein said add-on retractor element includes a flexible, elongate body member that slides around said first and second external surfaces and maintains positioning relative to said first and second retractor portions so that said body member spans a gap between respective ones of said first pair and said second pair of longitudinal edges as said first and second retractor portions are adjusted to separate from one another, wherein said body member of said add-on retractor element is elongated and extends between a distal end and an opposite proximal end, said body member further including opposite sides extending from said distal end to said proximal end, wherein said opposite sides define a first width of said body member at said distal end of said body member and said opposite sides define a second width of said body member at said proximal end of said body member, wherein said first width is greater than said second width.

14. The retractor assembly of claim 13, wherein:
wherein said first sidewall includes a u-shaped cross-sectional configuration between said first pair of longitudinal edges and said second sidewall includes a u-shaped cross-sectional configuration between said second pair of longitudinal edges; and said flexible body member of said add-on retractor element is wrapped partially around said first and second external surfaces of said first and second retractor portions.

15. The retractor assembly of claim 13, wherein said add-on retractor element includes a connection portion at a proximal end of said body member, said connection portion being mounted to proximal ends of said first and second retractor portions.

16. The retractor assembly of claim 15, wherein each of said first and second retractor portions includes an extension extending laterally from said proximal end of a respective one of said first and second elongate body and said connection portion is mounted to said extensions of said first and second retractor portions.

17. The retractor assembly of claim 16, wherein said connection portion includes an arm with a first portion extending proximally from a proximal end of said body member and a second portion extending laterally from said first portion to a mounting member of said connection portion that receives said extensions of said first and second retractor portions.

18. The retractor assembly of claim 17, wherein said mounting member includes a ring element defining an elongate passage oriented in a direction of translation of said first and second retractor portions relative to one another to increase said size of said working channel and said extensions move along said passage as said first and second retractor portions are translated relative to one another.

* * * * *